United States Patent
Grossman

(10) Patent No.: US 8,781,849 B1
(45) Date of Patent: Jul. 15, 2014

(54) SYSTEM FOR AND METHOD OF ENHANCING PATIENT'S HEALTHCARE BY UTILIZING PROVIDER-GENERATED DATA

(76) Inventor: Leonard Jesse Grossman, Netcong, NJ (US)

(*) Notice: Subject to any disclaimer, the term of this patent is extended or adjusted under 35 U.S.C. 154(b) by 0 days.

(21) Appl. No.: 12/462,798

(22) Filed: Aug. 10, 2009

Related U.S. Application Data

(60) Provisional application No. 61/087,656, filed on Aug. 9, 2008.

(51) Int. Cl.
G06Q 10/00 (2012.01)
G06Q 50/00 (2012.01)
G06Q 40/00 (2012.01)
G06Q 50/24 (2012.01)

(52) U.S. Cl.
CPC .................................... G06Q 50/24 (2013.01)
USPC ........................................ 705/2; 705/3; 705/4

(58) Field of Classification Search
CPC .................................................... G06Q 50/24
USPC ........................................................ 705/2–4
See application file for complete search history.

(56) References Cited

U.S. PATENT DOCUMENTS

| | | | |
|---|---|---|---|
| 2002/0046346 A1* | 4/2002 | Evans | 713/200 |
| 2002/0120471 A1* | 8/2002 | Drazen | 705/3 |
| 2004/0254816 A1* | 12/2004 | Myers | 705/2 |
| 2006/0036471 A1* | 2/2006 | Sanjay-Gopal et al. | 705/3 |
| 2006/0287879 A1* | 12/2006 | Malone | 705/1 |
| 2007/0088564 A1* | 4/2007 | March et al. | 705/2 |
| 2007/0136090 A1* | 6/2007 | Loutzenhiser et al. | 705/2 |
| 2008/0059224 A1* | 3/2008 | Schechter | 705/2 |

* cited by examiner

Primary Examiner — Joseph Burgess

(57) ABSTRACT

A system and method by which medical care providers enter data representing a patient's condition(s), treatments provided and drugs prescribed and other information that may be germane to a patient's condition. The data is transmitted to both a managed-care organization as well as to interconnected centralized service center(s) that receive similar data from multiple participating providers. The service center(s) store, for each patient, all the data. When such data is received from the medical providers treating the patient the service center can create a profile of the patient and compare all of this data with a database or lookup table (LUT) that contains all of the recommended protocols, treatments, follow-up treatments, medications, etc. for a patient. When follow-up treatments, medications, etc. are recommended, the service center(s) can automatically send reminders, recommendations or suggestions to the patient's provider(s) to take recommended steps to ensure the wellness of the patient.

16 Claims, 5 Drawing Sheets

SYSTEM FOR AND METHOD OF ENHANCING PATIENT'S HEALTHCARE BY UTILIZING PROVIDER-GENERATED DATA

CROSS-REFERENCE TO RELATED APPLICATION

This application is related to application Ser. No. 61/087,656 filed on Aug. 9, 2008, and claims priority on that application

BACKGROUND OF THE INVENTION

1. Field of the Invention

This invention generally relates to managed healthcare systems and procedures and, more particularly, to healthcare management systems and methods for enhancing patients' health by using existing provider Electronic Medical Records and/or billing data.

2. Description of the Prior Art

When a doctor or other medical "provider" examines or treats a patient, hand-written or electronic data records are generated and maintained in the office of the provider for future reference and treatment of the patient. The examination or treatment is typically followed by presenting the patient or the patient's insurance carrier with an invoice itemizing the services rendered and the procedures performed and the corresponding charges. Typically, arrangements are made for future visits, if necessary, so that additional treatments or procedures can be effected, generally in accordance with accepted medical practices. An insurance carrier or managed care organization ("MCO") responsible for payment for examinations and/or treatments, receive not only a statement of the charges but a complete breakdown of the treatments or procedures implemented as a backup for the monetary charges. Thus, the insurance companies, at least those that cover insured patients, are provided with extensive diagnostic and treatment information with regard to insured customers.

Insurance companies have obligations, real and/or perceived, in making sure that their customers are being provided with healthcare services that meet accepted medical standards. In an effort to discharge their obligations and establish good track records of patient care, MCO's utilize the billing data including diagnoses (ICD9's) and treatments (CPT's), to establish quality reports required by governmental agencies (i.e. HEDIS—to be discussed later). This data is limited in that it includes only billing data provided by one provider to one patient. It does not include any data provided by another unaffiliated provider or group of providers to the same patient. It does not include any medical or social information known by a provider that may exclude the need or rational for a given procedure or a contraindication for that procedure such as a previous complication thereto.

To supplement the reporting of the MCO's raw diagnostic and treatment data (ICD9 & CPT), and compensate for procedures and diagnosis provided to a single patient by other providers, or paid for by other MCO's whose data is not available to the reporting MCO, insurance companies routinely request additional information from providers. While many providers do cooperate and provide the MCO with the requested reports, many providers do not, or do so hesitantly because of the additional work, effort and expense in generating such reports by the providers and/or by their office staff. This additional monetarily uncompensated burden can create an adversarial relationship between insurers and providers.

As previously suggested, insurance carriers do have raw data they receive when providers submit requests for payments. However insurance companies have been slow to organize and distill such data because of the previously mentioned situation as well as the expense involved. Concerning the most complete collection of data in regards to any individual patient's care, there are no systematic collection procedures that assures that the providers and/or the insurance companies have all the relevant information, other than requests to providers which are frequently ignored, and costly site visits to provider offices and chart reviews by trained nursing personnel, which review is limited to that information about a patient available to a single provider that has or is to be paid for (covered) by that reporting MCO. This is a costly and inefficient method for the MCO's who must provide such data (HEDIS) to establish that they are providing quality health care to their insured, this data to be provided by mandate either to the federal government, health insurance department of state governments, and/or municipal governments.

Numerous patents have been issued covering various aspects of medical care and for handling provider invoices to insurance carriers or MCOs. Many of these patents are concerned with proper billing to the insurance companies and detecting improper bills. Thus, in U.S. Pat. No. 6,826,536 a healthcare billing monitor system for detecting healthcare provider fraud is disclosed. The patent disclosure is not concerned with the continued or ongoing wellness of the patient.

A system and methods for correlating medical procedures to medical billing codes is disclosed in U.S. Pat. No. 5,325,293, in which a system correlates billing codes with planned or performed medical procedures. The patent is primarily concerned with manipulating the raw codes to generate intermediate codes and the system is used to generate invoices.

A network-connected personal medical information and billing system is disclosed in the published U.S. patent application No. 2004/0254816. The method disclosed is used by a medical service provider to document and approve service and billing information substantially contemporaneously with the provision of services. The method also includes the storage of context information for output in connection with billing information.

In U.S. Pat. No. 5,191,522 an integrated group insurance information processing and reporting system is disclosed for processing and supervising a plurality of group insurance accounts. The system provides administration and actuarial functions.

Other patents disclose applications dealing with billing and insurance claims. In U.S. Pat. No. 6,026,363, systems and methods are disclosed for qualitative medical expressions. Typically, a phrase is used to generate a numerical value that represents the likelihood of an event. A database of information about the significance of the existence of a symptom for the diagnosis of a particular disease might then be predicted.

A medical history documentation system and method are disclosed in U.S. Pat. No. 5,704,371, in which information relating to at least one current medical condition of the patient is recorded. A physical examination, diagnosis and a treatment plan is shown.

In U.S. published patent application No. 2005/0065816 a healthcare management information system is disclosed in which a computer program generates a visual compliance display. The compliance obligation is typically received from a healthcare provider, the system automatically determining different compliance obligation levels.

U.S. Pat. No. 7,236,986 discloses a method of providing billing support in a high throughput to computer-aided detection environment, in which billing statements are generated using information relating to patient identification and film images from patients.

Other systems and methods have been disclosed for identification of clinical study candidates, such as the method disclosed in U.S. Pat. No. 5,191,522, in which a system searches electronic medical data to identify a pool of potential study participants. However, while the method may provide a pool of potential study participants for conducting tests and evaluations in connection with a given study it is not intended to directly benefit the wellness of any particular patient.

In U.S. Pat. No. 5,301,105 an all care management system is disclosed. The system integrates with the patient's healthcare provider, bank or other financial institution, insurance company, utilization review or an employer to provide the patient with pre-treatment, treatment and post-treatment healthcare and financial support. While the patent suggests post-treatment procedures, there is a little teaching in the patent of how such post-treatment procedures can or are to be accomplished. Additionally there is no teaching or suggestion in the patent or that billing information be analyzed, by the insurance companies or third-party service centers, for determining, for each patient, all of the services that have been performed on the patient and generating instructions, reminders or suggestions to the patients and/or providers to perform additional procedures, in accordance with well-established and accepted medical protocols, to complete the treatment protocols of the patient in order to assure the continued wellness of the patient.

SUMMARY OF THE INVENTION

Accordingly, it is an object of the invention to provide a system and method of enhancing patient's health in accordance with the present invention that do not have the disadvantages inherent in the systems and methods known in the prior art.

It is another object of the invention to provide a system and method of enhancing patient's health by using existing billing data generated by a provider to an insurance company or MCO.

It is another objective of the invention to provide a system and method of enhancing patient's health by using data generated by a provider as entry into an electronic health record (EHR), and/or other electronic practice management device.

It is still another object of the invention to provide a system and method as in the previous object that provide reports that suggest, request or require further, follow-up treatments and procedures by providers who have begun treating patients in order to complete suitable treatments based upon a comparison of procedures and treatments already provided and those in a reference database of accepted medical protocols.

It is yet another object of the invention to provide a system and method as in the previous objects that enhance the health of patients without imposing requirements for additional effort or work or expense by medical providers and/or managed care organizations or MCO's.

It is an additional object of the invention to provide a system and method of the type under discussion that generates and provides suggestions, reminders or requirements to medical providers to follow-up with accepted medical practices and procedures on the basis of a collective compilation of data generated by providers within a given practice, within a given municipality or region, within a state or within a country or even internationally, by analyzing or evaluating the billing and EHR data generated by billing and/or medical records software used by multiple providers and transmitted to multiple managed-care organizations by means of one or more service centers that receive the data and compare the procedures and treatments given to each individual patient with those procedures and treatments that should have been given or should be given in the future in order to complete the recommended or accepted medical regimens or protocols and to assure the wellness of the patient.

It is still a further object of the invention to provide the system and method of the type aforementioned that assist managed-care organizations in generating HEDIS reports, without further or ongoing assistance or input from medical care providers who have already identified procedures or treatments rendered to patients by entering this information into billing packages and/or medical records software used to transmit insurance claims and information to managed-care organizations or subsequently have submitted this information through electronic health records data in a coordinated effort to recognized service center(s).

In order to achieve the above objects, as well as others which will become evident hereinafter, the present invention involves a system and method by which medical care providers within a single practice, single community, statewide or nationally can enter data for a given patient identified by a unique identification number (ID). The data is formatted or otherwise includes information regarding both the patient's history, the patient's conditions, the procedures or treatments provided and the drugs prescribed and any other information that may be germane to a patient's general condition or wellness. The data may also include billing information intended to be transmitted by the billing software package, in a proper form, to the managed-care organization or insurance company. The data is retained by the medical provider but also transmitted to both a managed-care organization as well as to one or more interconnected centralized service centers that receive similar data from multiple providers participating in and using the system. The data, which includes the identity of a patient by means of a unique ID, may be encrypted before the data is transmitted from the service provider to the service center and/or the managed-care organization over open communication channels. The managed-care organization processes the data and reviews it in the normal course and issues payment to the provider in accordance with the rules and guidelines agreed-upon. The service center(s) on the other hand, store, for each patient ID, all of the data that bears on the patient's conditions, treatments, procedures received, medicines prescribed, and the like. When such data is received from one or more medical providers treating the patient the service center can create a profile of the patient's treatment history and is in a position to compare all of this data with a database or lookup table (LUT) that contains all of the recommended protocols, treatments, follow-up treatments, medications, etc. for a patient's given conditions and, on the basis of the patient's past medical history. When follow-up treatments, medications, etc. are recommended, the service center(s) can automatically send reminders, recommendations or suggestions to the patient's provider or providers to take any recommended future steps generally considered to be necessary or recommended to ensure the wellness of the patient. Such recommendations or suggestions can supplement the provider's own "tickler system" for generating reminders and follow-up notifications to patients for future treatment(s). However, in those instances where a provider's internal systems fail, where such systems may not be in place, or where a patient may be treated by more than one provider, a centralized database for generating such follow-up reminders to patients and/or providers can enhance patient health by essentially compiling and using existing information from data that has already been furnished to managed-care organizations and/or to service centers.

An inherent advantage of the present invention is that a central service center (MMQC), by compiling data from various providers including diagnoses (ICD9's), procedures (CPT's) as well as extractable information from electronic health records (EHR's), and e-prescribing (medications), could monitor overall quality of care and be in a position to report on pooled statistical data compiled by a multiple of providers to any individual patient. This MMQC would also be able to screen and monitor such data so as to be able to make ongoing recommendation for further patient monitoring and treatments, to both participating providers as well as to patients. Such recommendation could be based on standards of quality of care established by professional, specialty or governmental agencies. These recommendations can also be continuously updated as dictated by advancements in knowledge and technology. This would assure a better quality of care for patients whether insured by any particular MCO or not insured at all.

A BRIEF DESCRIPTION OF THE DRAWINGS

The novel features of the present invention, which characterize the invention, are set forth in the appended claims. The invention itself, however, both as to the system and method, and their modes of operation, together with additional advantages and objects thereof, will be best understood from the following detailed description of preferred embodiments, when read with reference to the accompanying drawings.

DESCRIPTION OF THE PREFERRED EMBODIMENTS

Figure 1:
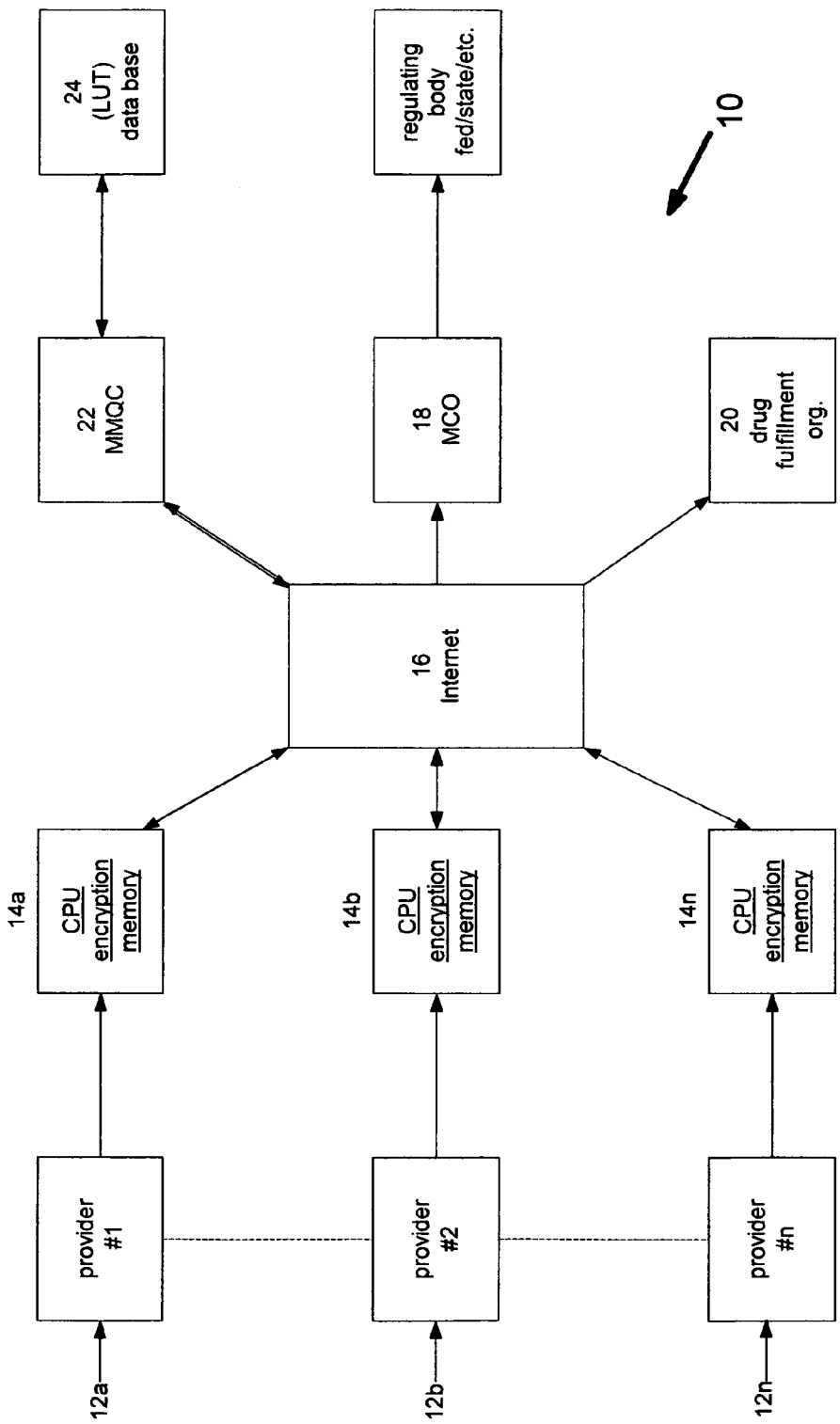
FIG. 1 is a block diagram illustrating one embodiment, by way of example, of a system architecture for implementing the present invention.

The invention will now be described with reference to FIGS. 1-3, in which identical or similar parts are designated by the same reference numerals throughout.

The primary purpose of the invention is to allow willing physicians, either individually or organized into an independent individual practice association (IPA) or any other organization of physicians or physician groups to pool existing and already collected patient data. Physicians can be organized within a single practice, regionally, statewide, nationally or internationally. By utilizing the system and method of the present invention, this will allow physicians or groups of physicians and the managed-care organizations (MCOs) with which they may have relationships, to deliver better quality patient care, regardless of the existence of insurance or nature of payment for services.

The method of the invention allows an easing of the administrative burden of providers by submitting on the provider's behalf data that is requested/required by the MCOs with which they have a relationship. This facilitation of transfer of comprehensive data to MCOs will enable the MCOs, in a more cost effective manner, to compile their required HEDIS reports to internal and external private and/or governmental agencies, facilities or quality-control groups. The invention will also make it possible for reports to be sent back to individual physicians with recommendations for follow-up patient management procedures, medications, or testing to enable health care providers to deliver a more consistent, cost-effective and better quality of patient care.

Referring to FIG. 1. An embodiment of a system in accordance with the present invention is generally designated by the reference normal 10. The system includes a plurality of participating providers 12a, 12b . . . 12n. Each provider has access to a computer terminal 14a, 14b . . . 14n, to be discussed more fully in connection with FIG. 2.

Each computer terminal is connected to a communication network. The specific network used is not critical for purposes of the present invention, and such networks may include, but not be limited to, the Internet, telephone networks, wireless, optical networks, local area networks (LANs), etc. In the embodiment illustrated in FIG. 1 each of the computer terminals is connected to the Internet 16. Such Internet access allows the terminals to selectively communicate with managed-care organizations 18 (MCOs) to submit reports and make claims for payment, to drug fulfillment organizations 20, and to one or more service centers 22 (MMQC), to be more fully discussed below, for monitoring quality of care. The MMQC has access to a database or lookup table 24 (LUT) in which there is stored information regarding medical practices and procedures approved and recommended by medical profession specialty societies and/or quality-control monitoring services or organizations. The managed-care organizations may optionally communicate with or be required to communicate with regulating bodies or agencies 26, at the regional, state or national level to provide quality control reports pursuant to HEDIS rules and guidelines.

Figure 2A:
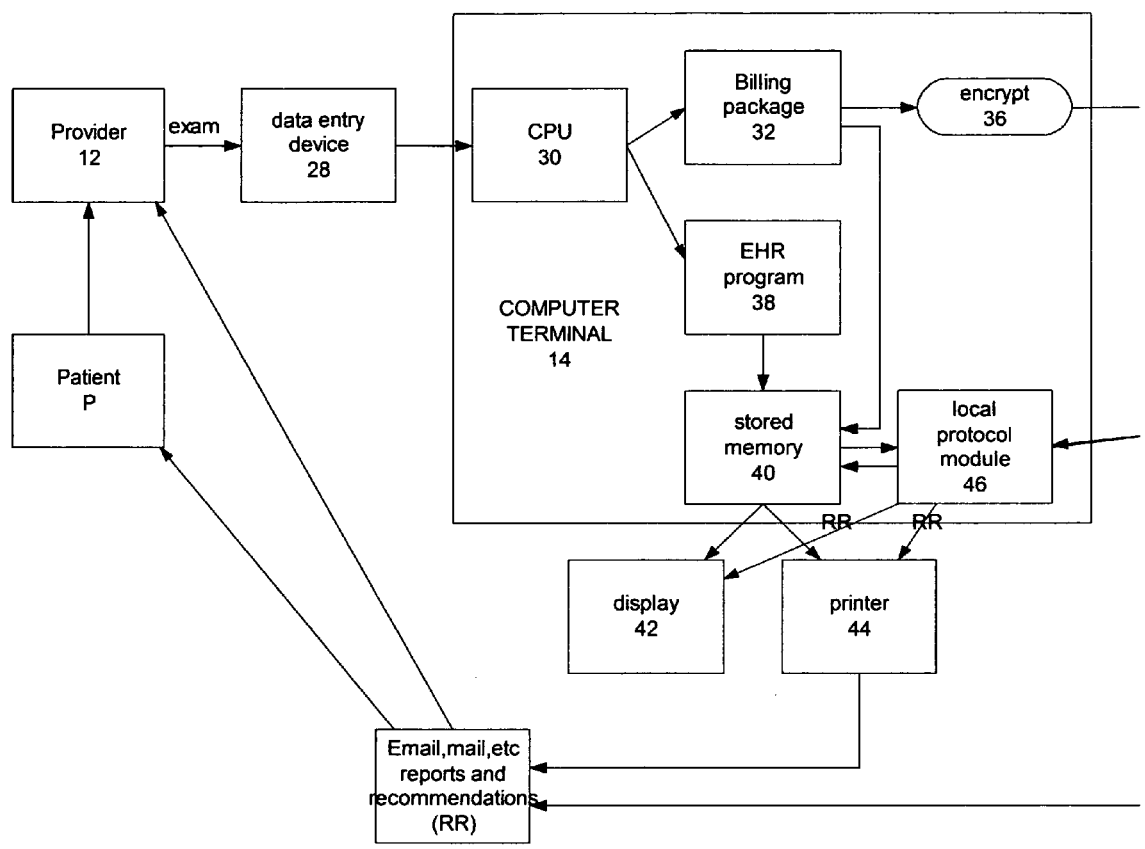
FIGS. 2A, 2B are similar to FIG. 1 for a single provider and providing additional details of a provider terminal that can be used with the system of FIG. 1.
Figure 2B:
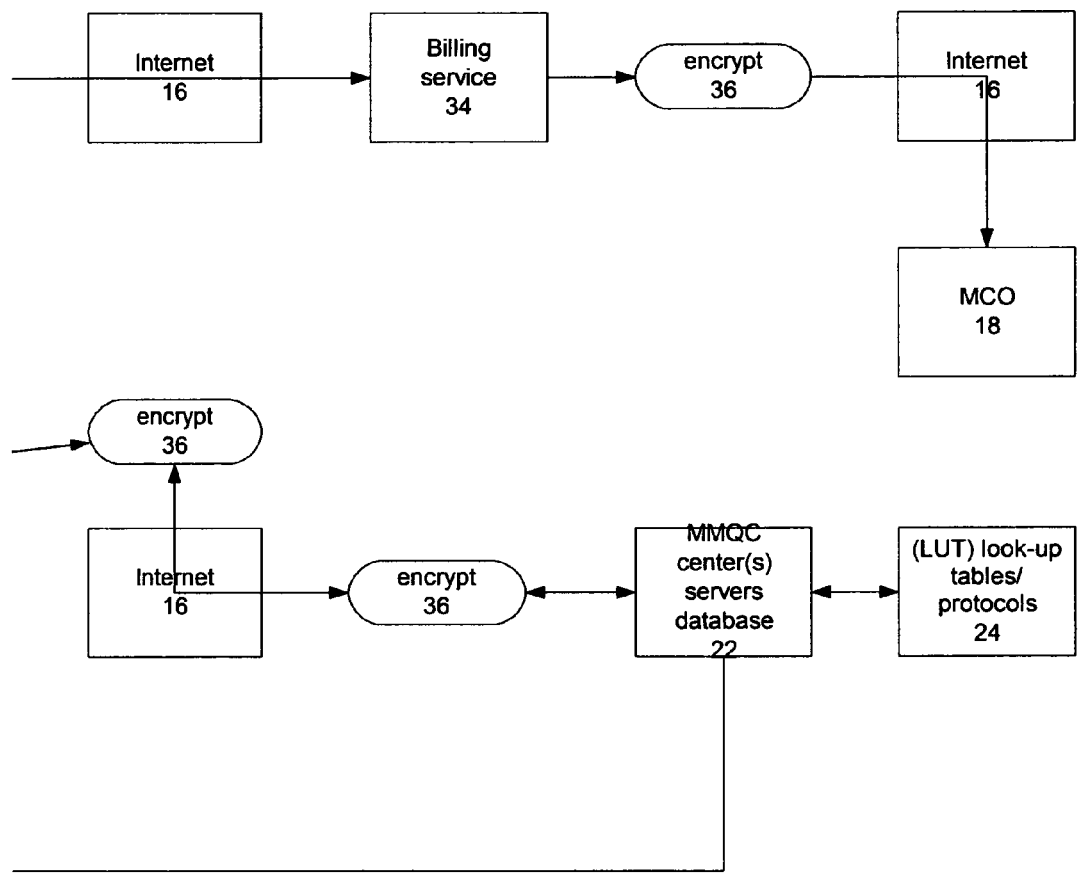

Referring to FIG. 2 a provider 12, upon examining and providing treatment to a patient P, enters by a data entry device 28, all data "D" appropriate to that medical encounter into the computer terminal 14. Whether the provider 12 enters the data directly or indirectly into the system is not important. However, the provider or his staff enters data into the computer terminal information regarding the patient's conditions, evaluations and treatments provided. This information is, according to the invention, converted by the system into one or more of the following types of codes, ICD-9, CPT, and HCPCS Level II codes. ICD codes are established in the International Statistical Classification of Diseases and Related Health Problems. ICD codes classify diseases and a wide variety of signs, symptoms, abnormal findings, complaints, social circumstances and external causes of injury or disease. Every health condition can be assigned a unique category and given a code. Such codes are typically up to six characters long and are revised periodically. Currently, the ICD is in its 10th revision, and an 11th revision is currently being revised to be specifically used in connection with Web applications. These codes are commonly referred to by most providers as ICD-9 codes, and will be referred to herein as such irrespective of the version or edition of the codes that are actually in use at any given time.

Examples of ICD-9 codes are:
V20.2 Routine healthy infant or child
V70.0 Routine normal medical examination (Adult)
010.0 Primary Tuberculosis infection
250.0 Diabetes Mellitus without complication
250.9 Iron Deficiency Anemia
345.1 Generalized Convulsive Epilepsy
346.0 Classical Migraine
455.0 Internal Hemorrhoids
595.0 Acute Inflammation of the bladder
651.0 Twin Pregnancy 780.50 Sleep Disturbance
787.0 Nausea & Vomiting
831.0 Dislocation of Shoulder Each year, in the United States, health care insurers process over 5 billion claims for payment. For Medicare and other health insurance programs to ensure that these claims are processed in an orderly and consistent manner, standardized coding systems are essential. The HCPCS (Healthcare Common Procedure Coding System) has been established for this purpose. The HCPCS is divided into two principal subsystems, referred to as level I and level II of the HCPCS. Level I of the HCPCS is comprised of CPT (Current Procedural Terminology), a numeric coding system maintained by the American Medical Association (AMA). The CPT is a uniform coding system consisting of descriptive terms and identifying codes that are used primarily to identify medical services and procedures furnished by physicians and other health care professionals. These health care professionals use the CPT to identify services and procedures for which they bill public or private health insurance programs. Decisions regarding the addition, deletion, or revision of CPT codes are made by the AMA. The CPT codes are republished and updated annually by the AMA. Level I of the HCPCS, the CPT codes, does not include codes needed to separately report medical items or services that are regularly billed by suppliers other than physicians.

Level II of the HCPCS is a standardized coding system that is used primarily to identify products, supplies, and services not included in the CPT codes, such as ambulance services and durable medical equipment, prosthetics, orthotics, and supplies (DMEPOS) when used outside a physician's office. Because Medicare and other insurers cover a variety of services, supplies, and equipment that are not identified by CPT codes, the level II HCPCS codes were established for submitting claims for these items. The development and use of level II of the HCPCS began in the 1980's. Level II codes are also referred to as alpha-numeric codes because they consist of a single alphabetical letter followed by 4 numeric digits, while CPT codes are identified using 5 numeric digits.

In October of 2003, the Secretary of HHS (Health and Human Services) delegated authority under the HIPAA legislation to CMS (Centers for Medicare and Medicare Services) to maintain and distribute HCPCS Level II Codes. As stated in 42 CFR Sec. 414.40 (a) CMS establishes uniform national definitions of services, codes to represent services, and payment modifiers to the codes. Within CMS there is a CMS HCPCS Workgroup which is an internal workgroup comprised of representatives of the major components of CMS, as well as other consultants from pertinent Federal agencies.

As noted previously, Current Procedural Terminology (CPT) codes consist of a listing of descriptive terms and identifying codes for reporting medical services and procedures performed by physicians and other health care providers. The purpose of these codes is to provide a uniformity to the description of medical, surgical, and diagnostic services and provide a reliable means of nationwide communications amongst providers, patients and interested third parties. In 2000 the CPT Code Set was designated by the Department of Health and Human Services as the national coding standard for physicians and other health care professional services and procedures under the Health Insurance Portability and Accountability Act (HIPAA). This mandates that CPT codes be used in all financial and administrative health care transactions sent electronically. CPT codes are updated annually by the American Medical Association (AMA).

Examples of CPT codes include:
99205 Office visit, new patient, prolonged
99239 Hospital discharge day management
27130 Total Hip replacement
32020 Insertion of Chest tube
47000 Biopsy of Liver
59514 Cesarean Delivery
67101 Repair of Retinal Detachment
71020 Chest X-Ray, 2 views
87088 Culture, Urine
97802 Medical Nutrition Therapy, initial evaluation Examples of (Healthcare Common Procedure Coding System) HCPCS Level II codes include:
A4206 Syringe with needle, sterile 1 cc
A7520 Tracheotomy tube, noncuffed
C1758 Catheter, urethral
E0112 Crutches, underarm, (pair)
J0170 Injection, Adrenalin up to 1 ml
K0001 Standard Wheelchair
L3070 Foot Arch Support
L8600 Implantable Breast Prosthesis
Q4011 Cast Supplies, Short arm case, pediatric
V2500 Contact Lens The providers key the codes into their computer terminals to inform the managed-care organizations of the conditions of the patients and to submit claims for charges to be reimbursed to the providers. When physicians submit claims to their participating managed-care organizations (MCOs) such data includes all pertinent CPT, ICD9, and HCPCS Level II codes needed for billing purposes.

When the data "D" is entered at 28, it is processed by a CPU 30. This data D is selectively processed within a billing package 32 in which the ICD9, CPT and HCPCS information "B" needed for billing purposes is converted into suitable form. Such existing medical billing, scheduling and reporting software programs as Lytec, Medical Manager, MDoffice, etc., or any other such proprietary package, can be utilized for formatting purposes. This formatted data B may then be encrypted at 36 and sent over the Internet 16 or any other suitable vehicle to a billing service 34. The entity 34 may be an independent "business associate" contracted for billing purposes, or an online billing service, such as Emdeon, Claim Remedi, etc., or an interactive program existing within the computer terminal 14. The data sent from the billing service 34 may then be encrypted 36, before it is released to the Internet 16 for transmission to the managed-care organization 18. The entered data D at 28 is processed and also sent to stored memory 40 to be added to data "E" also processed in an electronic health record program 38 (EHR) which collects data "C" including but not limited to all medical history and physical examination findings, procedures (billed or not billed), laboratory data, radiology tests, and consultation reports (ordered and/or reported) all of which is stored in memory 40. Any of the patients' data may be displayed on the computer terminal 42 or converted to a hard copy by means of printer 44. The stored memory composite data C interacts with a local protocol module 46 for giving the provider and/or his staff recommendations and reminders of treatments and follow-up care suggested for any given patient. This module 46 may simply include amongst other things, a docket or "tickler" system that arranges and tracks data input by the provider, and monitors for further timely actions. As an example, the local module could track all ordered tests, consultations, or future scheduled procedures or treatments and appropriately "flag" and report the incompletion of these entities until results are reported and acknowledged by the provider. Another main function of the local module is to constantly monitor and analyze data gathered from the provider with data supplied by a service center or centers 22 (MMQC), including referencing a database or lookup table 24 (LUT) for comparing the signs, symptoms, abnormal findings, complaints, conditions, administered procedures, etc. with protocols of accepted medical practices and follow-up treatments. Local module 46 is updatable and upgradable by encrypted interaction over the Internet 16 or other suitable vehicle with the service center 22 (MMQC). This interaction can make available to a provider, all pooled data collected by any and all other providers who utilize the invention that is stored in the folder of any patient identified by a given unique ID. Thus, the module 46 maybe in the nature of an intelligent knowledge base, embodying accepted, suggested or required medical procedures in connection with any medical conditions typically treated by the provider. The module 46 can provide amongst other things, reminders to the provider or his staff of suggested treatments or follow-up treatments appropriate for any given patient, or that reports of requested or ordered test or consultations have not been received or reviewed by the provider, or even that a procedure or test has already been performed by another provider. By utilizing pooled data, not only can redundancies be avoided, but a more comprehensive overview can be afforded to enable a more cost effective and better quality of care. Such reminders or suggestions may be communicated to the provider directly to his computer screen, or by means of printer reports, e-mails, voicemails, etc., sent by the module 46 to the provider and/or directly to the individual patient. Such reports may also be sent in any appropriate manner directly from the service center (MMQC).

Figure 3A:
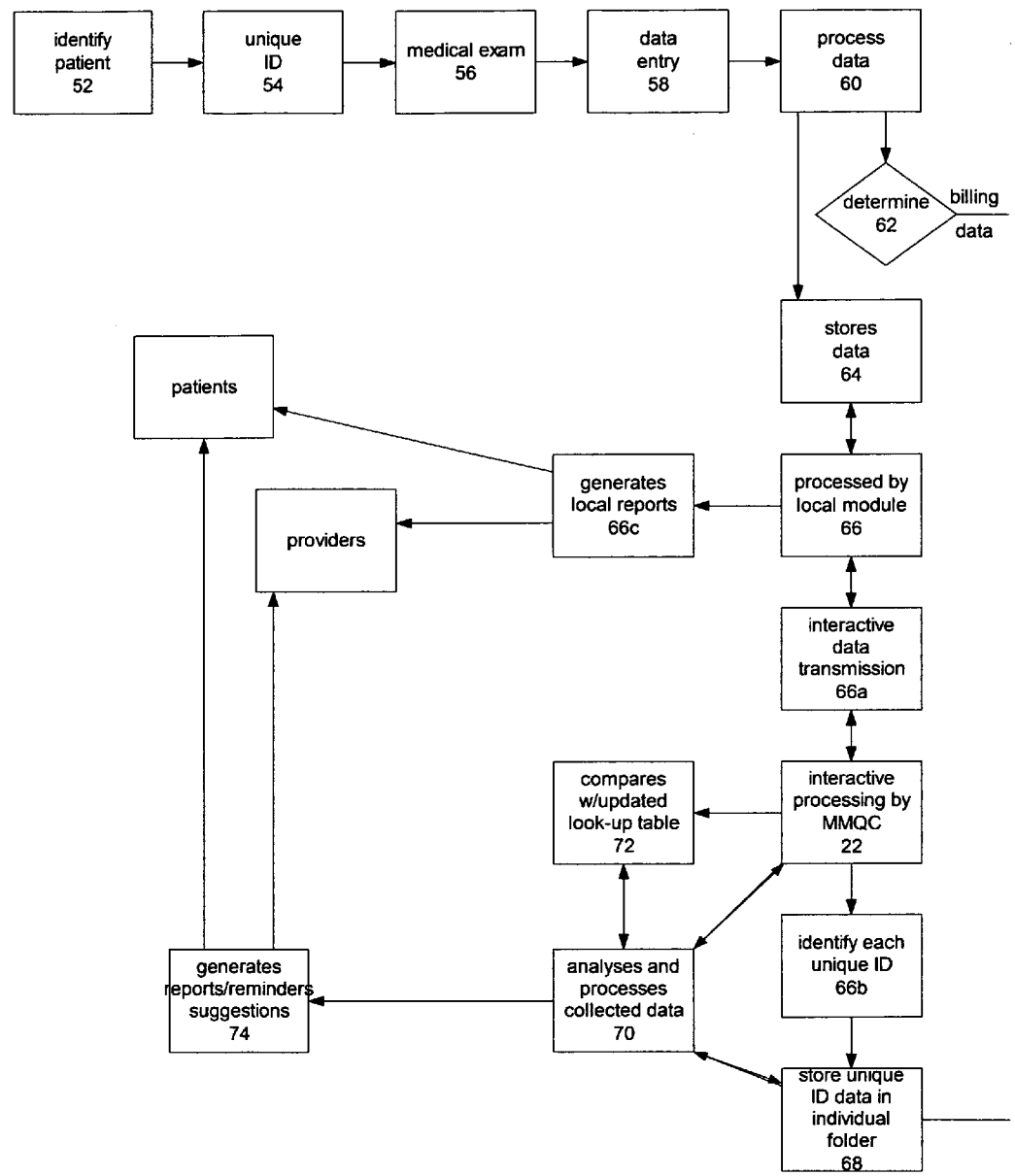
FIGS. 3A, 3B together form a flowchart outlining the method steps used to implement the invention with the system of FIG. 1 in accordance with one embodiment of the invention.
Figure 3B:
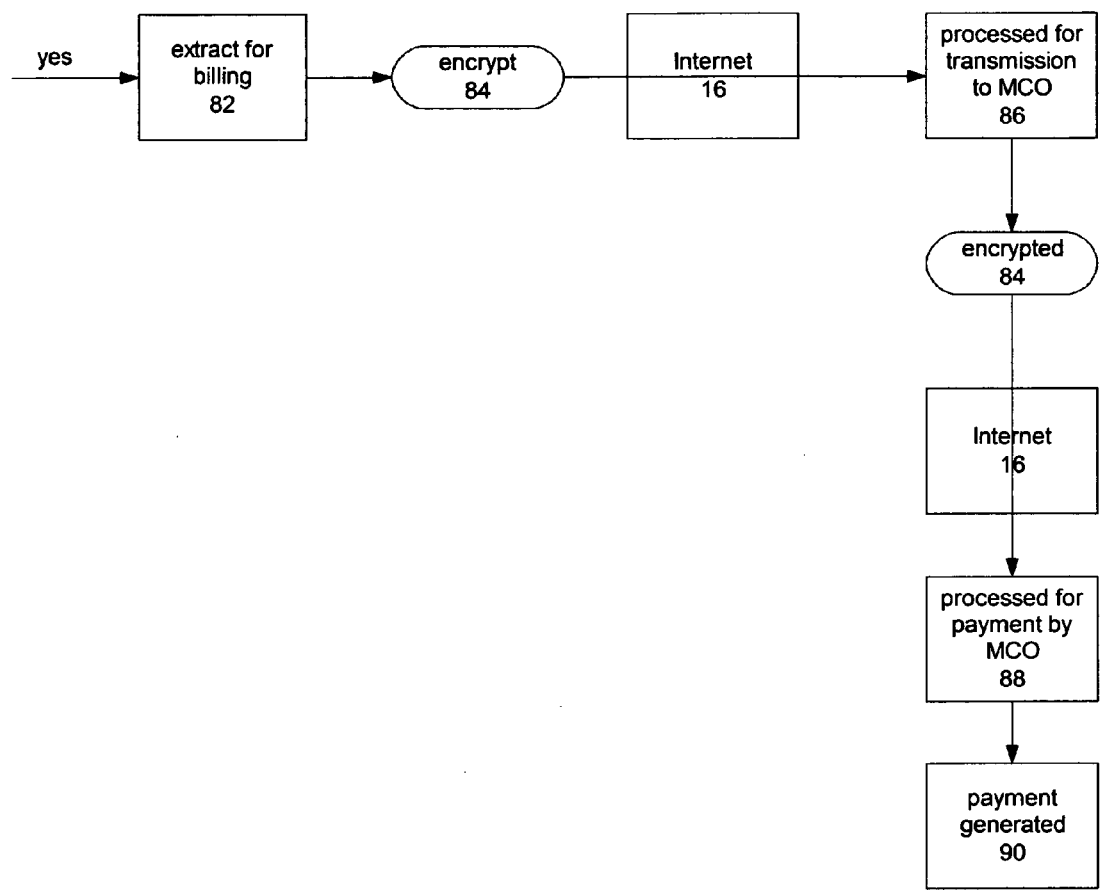
Figure 3B:
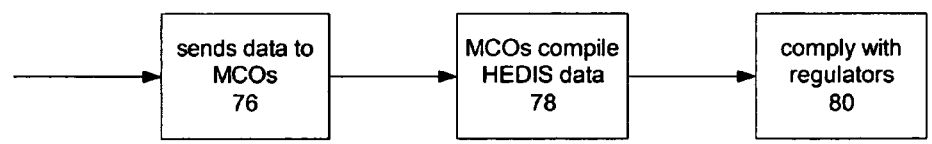

Referring to FIG. 3. a flowchart illustrates a typical flow of process steps 50 in accordance with an embodiment of the invention. Initially, a patient is identified, at 52. The providers or their staff associates the patient with a unique identification number (ID) 54. The ID or its format is not critical but must exclusively identify a patient so that it can uniquely identify a single patient over time amongst all providers and in all venues. For example, the ID may be a patient's Social Security number. However, such ID may also represent a specific aggregate of unique data that identifies a patient. Such a compilation may consist of an alphanumeric identifier drawn from known personal facts such as; last name, (maiden name), first name, middle initial, date of birth, time of birth, order of birth relating to multiple births, zip code of birth, hospital of birth, parents' last and first names, etc. If necessary, as a result of HIPAA regulations or guidelines, the patient's ID may also be encrypted before the information is transmitted outside of the offices of the provider were such information might be intercepted by third parties.

During or after a patient examination has taken place, at 56, the provider or providers or their staff enter data 58 ("D") into the computer terminal. Such data D, as indicated, may include appropriate ICD and CPT codes, consistent with the codes in existence at the time, or as may be agreed upon based on standards in use for submission to managed-care organizations to which payment claims are to be made. It also includes electronic healthcare data including but not limited to all medical history and physical examination findings, procedures (billed or not billed), and laboratory data, radiology tests, and consultation reports (ordered and/or reported). This combined data is processed at 60 by the billing package 32 and the EHR program 38. At 62 a determination is made as to whether health insurance is to be billed. If health insurance is to be billed for services, the appropriate billing information "B" is further processed and extracted at 82 by the billing package (32) and this data can be encrypted at 84 to be transmitted over the internet 16 or other suitable vehicle to a billing service (34) to be further processed at 86 into a format acceptable for transmission to managed care companies. After this processing, the data B can be again encrypted 84 and sent over the internet 16 to MCOs. Here the data is processed for eligibility and amount of payment 88 and payment 90 is generated to the provider.

When insurance is not to be billed B=0 and C=E. When insurance is to be billed (B≠0), the ICD9, CPT, and HCPCS data processed by module (32) is added to data processed by an electronic health record program (38) and thereby all appropriate data E+B collected is entered into a local electronic health record and stored in memory 64. This combined data C=E+B (or B=C–E) undergoes interactive processing with a local protocol module 66 from which local reports and suggestions can be generated to providers and patients 66c. The data and processing protocols of module 66 is updated and upgraded as appropriate by an ongoing and interactive transmission 66a through a secure connection with MMQC 22. Data is encrypted and transmitted through the interne 16 or other suitable vehicle and all data is interactively processed by MMQC 22. The data received by the service center 22 pertaining to a given patient associated with the transmitted unique ID from any provider or group of providers at any and all locations, is identified at 66b and compiled and stored in a patient's folder or electronic file, at 68. At 70, the service center analyzes and processes all of the data in each unique folder 68 which contains information including but not limited to each patient's history, including signs and symptoms, ICD, CPT, and HCPCS data, laboratory and radiology requests and reports, medications, treatments and recommendations. An important feature of the invention is that the patient's folder is continuously or regularly compared at 72 with an updatable database or look up table (LUT) of medical protocols defining accepted medical practices and follow-up treatments in connection with any condition and/or ICD9 data provided by the providers. This LUT is in the form of a knowledge base that is continuously updated with procedures, treatments and recommended follow-up protocols developed and established in accordance accepted practices of quality medical care. Such medical protocols may be developed with the input of medical associations, specialty organizations, governmental and regulatory organizations. After the reference database (LUT) is accessed and a determination is made as to what form and when the next follow-up care of the patient should be, the service center through its interactive network, creates a report of suggested, recommended or required follow-up procedures, at 74. Such recommendations, suggestions, etc. are transmitted in a suitable form to the provider or providers of the patient, and or reminders directly to the patient to insure optimal patient care. Each folder is also searchable, within the restraints of HIPAA laws, to access any and all patients with any predefined criterion. This is not only of potential benefit on any individual patient basis, but also on a public health basis, wherein pooled data may be presented on a statistical and anonymous basis.

Whether or not insurance claims are to be made, and irrespective of whether managed-care organizations are in anyway involved with regard to any given patient, the service center 22 receives and organizes the data received from all participating providers. As suggested, the incoming data may be from providers or physicians in a single practice, or providers or physicians that have agreed or are required to participate on a local, regional, national or even international level.

Pooled data collected on any given patient identified by a single unique ID at 68, if requested by the provider and/or the managed care company (MCO), and as allowed by HIPAA regulations, can be encrypted and sent over the internet or other appropriate vehicle to the MCO's so that they may utilize this data 76. This data may be compiled, at 78, by the MCOs to enable more complete and accurate HEDIS report to be generated, at 80, in compliance with appropriate rules and regulations. HEDIS represents "Health-Care Effectiveness Data and Information" which is a widely used performance measure in the managed-care industry, developed and maintained by the National Committee for Quality Assurance (NCQA). HEDIS was designed to allow consumers to compare a healthcare plan's performance to other plans at the national or regional level. HEDIS reports are increasingly used to track the year-to-year performance of managed care organizations. HEDIS is one component of NCQA's application process, although some plans submit HEDIS data without seeking accreditation. An incentive for many health plans to collect HEDIS data is that it is a Centers for Medicare and Medicaid Services (CMS) requirement that health maintenance organizations submit Medicare HEDIS data in order to provide HMO services for Medicare patients. HEDIS measures are divided into a number of categories, including effectiveness of care, availability of care, satisfaction with the experience of care, health plan stability, user services, cost of care, etc. Such measures are added, deleted and revised annually. For example, increased attention to medical care for seniors has prompted the addition of measures related to glaucoma screening and osteoporosis treatment for older adults. Of the health-care concerns covered by HEDIS are immunizations, cancer screenings, treatment following heart attacks, diabetes, asthma, flu shots, access to services, dental care, alcohol and drug dependence treatment, timeliness of handling claims and phone calls, prenatal and postpartum care, mental health care, work care and preventive visits, in-patient utilization, drug utilization and distribution of members by age, sex, etc. The measures in 2007 addressed potentially harmful drug-disease interactions in the elderly, relative resources used for diabetes, asthma and acute low back pain.

Traditionally, HEDIS data are collected through surveys, medical chart reviews, and insurance claim data for hospitalizations, medical office visits and procedures. Surveys must be conducted by an NCQA-approved external survey organization. Clinical measures use administrative or hybrid data collection methodology. Administrative data are electronic records of the services, including insurance claims and registration systems from hospitals, clinics, medical offices, pharmacies etc. For example, one measured condition is childhood immunization status. This requires health plans to identify two-year-old children who have been enrolled for at least one year. The plan reports the percentage of children who received specified immunizations. Plans may collect data for this measure by reviewing insurance claims and immunization records, but this method will not include immunizations received at community clinics that do not or cannot submit insurance claims, or immunizations that may have been provided and paid for by a different provider or health plan. For this measure, plans select a random sample of the patient population and supplement claims data with data from on site medical record reviews. By doing so, plans may identify additional immunizations and report more favorable and accurate rates. However, such methods are costly, time-consuming and require nurses and trained medical record reviewers authorized to review confidential medical records. Then, to the extent that such data collection has been based on requests to providers, acquisition of such data has met with limited success. Medical providers, who are already overburdened with existing administrative regulations and an excessive burden of medical reporting, besides the necessity of dealing with managed-care organizations for making claims, etc., have little incentive to utilize their own resources at their own expense, including staff and time of the provider, to compile and transmit such data to the many insurance companies with which they must affiliate. Such HEDIS data may be easily evaluated, compiled, and accurately extracted from the data submitted to a service centers (MMQC), or a compilation of service centers which form an integral part of the invention. Thus the invention allows managed-care organizations not only to obtain HEDIS information so that they can satisfy their own HEDIS compliance requirements, but to improve the overall level of patient care. By interfacing the patient data with a knowledgeable in the form of a lookup table, for example, providers and/or patients can be reminded or requested to follow-up with additional treatment or care to improve overall quality of patient care.

HEDIS reports are important to managed-care organizations or HMOs, not only because they are a component of becoming accredited, but also because this data is used for marketing with employers, consultants and insurance brokers who purchase health insurance for groups. NCQA's web site for example, includes a summary of HEDIS results compiled by managed-care organizations. Such data is regularly published at least once annually and is available for review on the Web. Local business organizations, government agencies and media report HEDIS results annually. Many managed care organizations or HMOs publish their HEDIS annual reports on their web sites in an effort to establish their effectiveness and to market their managed-care organizations. HEDIS data is used as a national standard for measuring performance of managed-care organizations. Managed care organizations are also required by state law to collect such data to establish minimum standards of network adequacy and quality of care in order to be licensed. The State of Montana, for example, requires such reporting. Therefore, while it is important and in the best interest of MCOs to collect data required for effective HEDIS reporting, it is a responsibility that requires significant resources.

With the present invention, the service center 22 can receive, store, process, and readily provide data to health care organizations on an individual patient basis, to the extent allowed by HIPAA laws, to better enable them to generate HEDIS reports on the basis of information reported not only by a single provider, but by multiple providers within a medical practice, regional, state, national or international cooperative. This better enables all of the relevant data with regard to any single patient associated with a given patient ID to be included. In this way, whether a patient is treated by one provider or a number of providers, the service center or centers 22 are in a position to provide complete information with respect to each patient, whether covered by an insurance company or not. The invention, therefore, provides a significant benefit to managed-care organizations in that in its utilization, an extensive and costly responsibility of theirs can be readily implemented at little or no cost to them. Insurance companies, therefore, should have an incentive to encourage providers to convert their computer terminals to include billing modules and EHRs of the type discussed above and to encourage the development of service centers (MMQCs). This can not only provide necessary HEDIS data, but assures better follow-up patient care. The more complete the patient data collection and the better that follow-up care is provided to a patient, the better the report cards are to managed care organizations. Whether the managed care organizations encourage the development of MMQCs to enable them to achieve better HEDIS reports or because they are required to do so by quality control regulatory agencies, and/or to enhance their own image in order to become more competitive in relation to other managed-care organizations with which they compete, it is clearly in the best interest of quality patient care, even if the patient is not covered by insurance.

As will be appreciated, sensitive patient information needs to be safeguarded from unauthorized third parties. The Health Insurance Portability and Accountability Act of 1996 (HIPAA), is intended to insure the privacy of patients. It is for this reason, therefore, that the data is preferably encrypted at 36, in FIG. 2, and elsewhere before it is transmitted over the Internet or other suitable medium. The major goal of such privacy rules is to assure that individual health information is properly protected while allowing the flow of such health information needed to provide and promote high quality health care and to protect the public's health and well-being. The HIPAA rules, therefore, strike a balance that permits important uses of information while protecting the privacy of people who seek care. The rules, however, are intended to be flexible and comprehensive to cover a variety of uses of disclosures that need to be addressed. The privacy rules apply to health plans, health care clearinghouses and to any health care provider who transmits health information in electronic form in connection with transactions adopted under the standards of the HIPAA. Every health care provider, regardless of size, who electronically transmits health information in connection with certain transactions, is a covered entity. These transactions include claims, benefit eligibility, referral authorization requests or other transactions for which standards have been established under HIPAA. Thus, the privacy rules cover health care providers whenever data is electronically transmitted, such as transactions sent directly to a billing service as a third-party, to process data on their behalf. However, in general, a "business associate" under the HIPPA guidelines is a person or organization, other than a member of a covered entity's workforce, which performs certain functions or activities on behalf of, or provides certain services to, a covered entity that involves the use or disclosure of individually identifiable health information. "Business associate" functions or activities on behalf of a covered entity include claims processing, data analysis, utilization review and billing. Therefore, business associate services to a covered entity are limited to legal, actuarial, accounting, and consulting, data aggregation, management, administrative, accreditation or financial services. A covered entity can be the business associate of another covered entity. When a covered entity uses a contractor or other third-party to perform "business associate" services or activities, it is required that the covered entity includes certain protections for the information in a business associate agreement, so that it remains protected. A covered entity may not contractually authorize its business associate to make any use or disclosure of protected health information that would violate HIPAA rules. With the present invention, the service provider or providers (MMQC) 22 may be qualified as business associates under the HIPAA rules so that sensitive health care information to perform the services discussed, including treatment, payment and health care operations can occur. Health care operations may include, for example, quality assessment and improvement activities, including case management and care coordination; competency assurance activities including provider health plan performance evaluations, conducting or arranging for medical reviews, ordinance or legal services including fraud and abuse detection and compliance programs; business development, management and administration, and general administrative activities including, but not limited to, protecting health information, creating limited data set and certain fundraising for the benefit of the covered entity.

Therefore, while the present invention generates and transmits patient sensitive data, such activities are consistent and in compliance with the HIPPA guidelines, particularly if the data is fully encrypted prior to dissemination over the Internet or other communication network, or another acceptable secure vehicle is utilized.

A feature of the invention, therefore, is to utilize, analyze and report on data C already being input into an existing electronic health record and an existing practice management or billing package or module. This same data is utilized to monitor the performance of participating health care providers and report back to them thus enabling them to assure compliance with existing and developing standards of care established by appropriate professional medical organizations, as well as with governmental and regulatory standards. This collection of data will include but is not limited to procedures (CPT's), diagnoses (ICD9's), HCPCS Level II, drug utilizations (e-prescribing), data collected through patient records (EHR's) including laboratory and radiology test requests and reports, consultation requests and reports, and other modalities of patient care.

This collection of this data C will be of benefit to health care providers by enabling them to ensure quality care as well as follow-up care to their patients. Built into computer databases is the ability to flag (alert) the provider to the existence of any condition that might require further diagnostic investigation or treatment. This would also enable the collection of pooled data submitted by individual and any group or groups or the totality of complying providers to enable the compilation of data that would be of public interest and benefit.

Typical examples of the utility of the invention include:
- In obtaining a pediatric history, if developmental criteria is recorded and transmitted, and certain developmental milestones are delayed, an alert would be generated to the provider suggesting further evaluation.
- If there is a family history of cancer or previous patient history of cancer, and an appropriate screening test has not been performed in a reasonable time, an alert to suggest such a screen will be generated.
- If a patient smokes, and a smoking cessation program had not been recommended, an alert to propose a smoking cessation program would be generated.
- In compiling the immunization record of an individual pediatric patient, the existence of vaccines given by other providers would be known even if the caretaker was unaware of it.
- Public health data regarding the incidence of diseases, by age and/or pre-existing condition (i.e. high blood pressure) and or existing condition (i.e. smoker) can be easily gathered and utilized for the public good.

MMQC will benefit the provider by generating practice care data (HEDIS) reports on behalf of the provider to appropriate managed care organizations (MCO's). The HEDIS reports are required by MCO's and are becoming more important and an ever increasing burden to the provider. This adds to the adversarial conditions existing between providers and MCOs.

By encouraging the use of lower cost (generic) medications and implementing other economies at the point of care, cost savings as well as the other abilities of the MMQC to benefit overall quality of patient care will enable providers who participate with service centers (MMQCs) to negotiate on their own behalf for better contracts and reimbursements with the MCOs.

MMQC would benefit the Managed Care Organizations in as much as it would ensure more cost effective, accurate and timely HEDIS reporting which is becoming more costly for MCO's in that it requires extensive manpower to obtain. Such data also is becoming harder to obtain because of the frequent adversarial conditions existing between providers and MCOs. This invention will also enable cross referencing of a given patient's records with his various providers allowing more complete reporting and the elimination of redundancies. By utilizing MMQC 22 data, the provider will be encouraged to consider lower cost medications and therapeutic modalities. This would be an added benefit to MCO's and encourage their compliance to better contracting with participating providers, which would lessen the adversarial conditions between MCO's and providers. This advantage to MCO's might make them more willing to negotiate even with groups of physicians not billing under a single Tax ID, as for example a hospital affiliated Individual Practice Association (IPA). The existence of an MMQC will enable providers and encourage MCO's to negotiate;

1. On an individual basis.
2. Through Individual Practice Associations (IPA's)
3. Through Hospital—Physician joint ventures (PHO's)
4. Through groups billing under a single tax ID.

In essence the purpose of the MMQC in accordance with this invention is to utilize data that is already in existence, in a manner that can enable the provider to deliver better quality and cost effective care to patients, and at the same time easing some of the extra burden in manpower and time that that is being imposed not only by the correlation of care between various providers of the same patient, but by easing the burden of reporting required to be generated by providers. The benefit to MCO's will be a significant improvement in HEDIS compliance as well as cost savings in data gathering and quality review. All this will enable better relations with providers through negotiation. This system also makes it more likely that patients, who move between healthcare providers or between different healthcare systems, or to another geographic location, will continue to receive appropriate and monitored care. Also, the invention will allow providers and their patients complete and accurate historical data, ultimately resulting in a higher quality, more cost effective care to patients.

It is practical, customary and accepted practice that a provider submits for billing purposes to the managed care companies only the main and most pertinent ICD-9 codes to support adequate reimbursements. It should be noted that system codes pertinent and related to the main diagnosis are often omitted when codes are submitted for payment to MCO's. For example a patient diagnosed with infectious mononucleosis will most likely be submitted for billing purposes with only the ICD-9 075 (mononucleosis). The patient very likely was complaining of sore throat (ICD-9 463), Difficulty swallowing (ICD-9 782.20), malaise and fatigue (ICD-9 780.7), and fever (ICD-9 780.6), and headache (ICD-9 784.0). On examination the patient with infectious mononucleosis may likely to be found to have swollen neck lymph nodes (ICD-9 785.6) and an enlarged spleen (ICD-9 789.2). These latter diagnoses most likely will not be recorded for billing purposes. It is the intention of this invention to develop the ability to incorporate the inclusion of these signs and symptoms either by their ICD-9's codes or any other easily utilizable modality to lift such data from various EHR's to better enable their inclusion into the databases of this invention. This will construct a more accurate and complete historical record and enable the generation of better analysis and recommendations for follow up of patient care.

The invention contemplates that more than one service center may be established especially at the inception of its implementation. These centers will be or eventually will be interconnected so as to share a totality of data. In compliance with HIPAA laws, each provider utilizing the system will apply for and be assigned, where appropriate, an approved provider ID that will grant access to all necessary data pertaining to any patient under that provider's care.

Though the present invention was shown and described with references to the preferred embodiments, such is merely illustrative of the present invention and is not to be construed as a limitation thereof, and various modifications of the present invention will be apparent to those skilled in the art. It is, therefore, not intended that the present invention be limited to the disclosed embodiments or details thereof, and the present invention includes all variations and/or alternative embodiments within the spirit and scope of the present invention.

What is claimed is:

1. A method of enhancing patient's healthcare comprising the steps of:
   a. identifying a patient characterized by a unique identifier;
   b. inputting contemporary patient data "D" by a health care provider for a patient reflecting a patient's visit to a health care provider including all available codifiable personal and medical data into a computer terminal having access to established medical codes that characterize a patient's codifiable data including all input signs, symptoms, findings, diagnoses, treatments and procedures, said data D including billing data "B" when required for billing or expensing purposes;
   c. automatically converting by said computer terminal, without additional effort or work by the healthcare provider, all codifiable patient data D input by the health care provider into corresponding medical codes "C" of said established medical codes representative of all of a patient's contemporary personal and medical data "D" associated with a contemporary visit to a health-care provider into a computer terminal of a data processing system that includes communication means for communicating with and accessing said central processing center, said data C including said data B identified by the health care provider as being required to be submitted for payment or reimbursement to an insurance carrier or HMO while data E=C−B not requiring identification by the health care provider, wherein C−B>0;
   d. collecting and maintaining all said contemporary data C and previously entered and saved patient coded data in said central processing center, for said patient and other patients, representative of all entered patient data, in a first database at said central processing center to provide cumulative or composite coded data for said patient and other patients indicating all available and codifiable data including past and present signs, symptoms, findings, diagnoses, treatments and procedures independently of specific healthcare providers or sources of such patient data;
   e. maintaining a second database at said central processing center of recommended medical protocols and guidelines for treatment and follow-up patient medical care based on all said input signs, symptoms, findings, diagnoses, treatments and procedures; and
   f. electronically evaluating said cumulative coded data C of signs, symptoms, findings, diagnoses, treatments and procedures for said patient and comparing it with said medical protocols and guidelines within said second database to establish recommended follow-up care for said patient based on updated data collected in said first database for said patient independently of which previous health-care providers entered the medical data and when or where said patient's data had been previously entered into said first data base;

g. issuing notification of recommended generally accepted medical evaluations, procedures, and treatments for subsequent follow-up care based on said cumulative or composite coded data to at least one of a patient, a patient's health-care provider, and/or a patient's managed care organization (MCO) by means of at least one of: an electronic transmission to a computer terminal, a notification sent by postal service or a telephonic communication; and h. providing global access to said patient's cumulative or composite coded data and medical information to any patient's authorized medical or health care provider independently of when, where or by whom the previous patient data was entered.

2. A method as defined in claim 1, wherein said converting step comprises converting, said contemporary information including signs, symptoms, findings, diagnoses, treatments and procedures entered by a provider, into a plurality of said established medical codes suitable for transmission to said central processing center.

3. A method as defined in claim 2, wherein said health-care provider who enters said contemporary personal and medical data during said patient's examination is provided with contemporaneous feedback and notification on the basis of said patient's contemporary and saved codified historical medical data and said recommended medical protocols and guidelines suggesting at least one of additional medical procedures, tests and medications for administration contemporaneously with the medical examination of said patient.

4. A method as defined in claim 1, wherein said codes include the same established medical codes used by the health-care provider to be transmitted to said patient's managed care organization (MCO).

5. A method as defined in claim 2, wherein said established medical codes include at least one of ICD, CPT and HCPCS codes that characterize a patient's codifiable data reflecting the entirety of the evaluations and treatments of said patient.

6. A method as defined in claim 2, wherein all medical data including signs, symptoms, findings, diagnoses, treatments and procedures entered by a health care provider is converted by said computer terminal, without additional effort or work by the healthcare provider, into one of at least ICD, HCPCS and CPT codes.

7. A method as defined in claim 1, further comprising the step of periodically updating said recommended medical protocols and guidelines.

8. A method as defined in claim 1, further comprising the step of preparing HEDIS reports on the basis of codified cumulative or composite coded data stored in said first data base.

9. A method as defined in claim 1, further comprising the step of archiving all of said cumulative or composite coded data for future analysis.

10. A system for enhancing patient's healthcare comprising:

a. means for identifying a patient characterized by a unique identifier;

b. means for inputting contemporary patient data "D" by a health care provider for a patient reflecting a patient's visit to a health care provider including all available codifiable personal and medical data into a computer terminal having access to established medical codes that characterize a patient's codifiable data including all input signs, symptoms, findings, diagnoses, treatments and procedures; said data D including billing data "B" when required for billing or expensing purposes;

c. means cooperating with the computer terminal for automatically converting without additional effort or work by the healthcare provider, all available codifiable patient data D input by the health care provider into corresponding medical codes "C" of said established medical codes representative of all of the patient's codifiable signs, symptoms, findings, diagnoses, treatments and procedures representing said patient's contemporary personal and medical data "D" associated with a contemporary visit to a health-care provider into a computer terminal of a data processing system that includes communication means for communicating with and accessing said central processing center, said data C including said data B identified by the health care provider as being required to be submitted for payment or reimbursement to an insurance carrier or HMO while data $E=C-B$ not requiring identification by the health care provider, wherein $C-B>0$;

d. means for collecting and maintaining all said contemporary data C and previously entered and saved patient codifiable data in said central processing center, for said patient and other patients, representative of all entered patient data, in a first database at said central processing center to provide cumulative or composite coded data for said patient and other patients indicating all available and codifiable data including past and present signs, symptoms, findings, diagnoses, treatments and procedures independently of specific healthcare providers or sources e. means for maintaining a second database at said central processing center of recommended medical protocols and guidelines for treatment and follow-up patient medical care based on all said input signs, symptoms, findings, diagnoses treatments and procedures; and f. means for electronically evaluating said cumulative or composite coded data C of signs, symptoms, findings, diagnoses, treatments and procedures for said patient and comparing it with said medical protocols and guidelines within said second database to establish recommended follow-up care for said patient based on updated data collected in said first database for said patient independently of which previous health-care providers entered the medical data and when or where said patient's data had been previously entered into said first data base;

g. means for issuing notification of recommended generally accepted medical evaluations, procedures, and treatments for subsequent follow-up care based on said cumulative or composite coded data to at least one of a patient, a patient's health-care provider, and/or a patient's managed care organization (MCO) by means of at least one of: an electronic transmission to a computer terminal, a notification sent by postal service or a telephonic communication; and h. means for providing global access to said patient's cumulative or composite coded data and medical information to any patient's authorized medical or health care provider independently of when, where or by whom the previous patient data was entered.

11. A system as defined in claim 10, wherein said means for collecting, includes means for archiving all of said cumulative or composite coded data for future analysis.

12. A system as defined in claim 10, wherein said computer terminals are programmed to convert, without additional effort or work by the healthcare provider, all medical data input including signs, symptoms, findings, diagnoses, treatments and procedures for which a code has been previously established, into ICD, HCPCS and CPT codes.

13. A system as defined in claim 10, wherein said established medical codes additionally include at least one of ICD, CPT and HCPCS codes.

14. A system as defined in claim 13, wherein main or pertinent billing codes and all additional codes not used for billing purposes are established representative of signs, symptoms, findings, diagnoses, evaluations and treatments.

15. A system as defined in claim 14, wherein said codes are representative of contemporary data.

16. A system as defined in claim 14, wherein said codes are representative of historical data.

\* \* \* \* \*